(12) United States Patent
Lynn et al.

(10) Patent No.: US 7,255,991 B2
(45) Date of Patent: Aug. 14, 2007

(54) TEMPLATE-DRIVE PROCESSES FOR SYNTHESIZING POLYMERS AND COMPONENTS RELATED TO SUCH PROCESSES

(75) Inventors: David Lynn, Atlanta, GA (US); Xiaoyu Li, Cambridge, MA (US)

(73) Assignee: Emory University, Atlanta, GA (US)

( * ) Notice: Subject to any disclaimer, the term of this patent is extended or adjusted under 35 U.S.C. 154(b) by 343 days.

(21) Appl. No.: 10/396,001

(22) Filed: Mar. 24, 2003

(65) Prior Publication Data

US 2003/0215853 A1 Nov. 20, 2003

Related U.S. Application Data

(60) Provisional application No. 60/366,870, filed on Mar. 22, 2002, provisional application No. 60/420,533, filed on Oct. 23, 2002, provisional application No. 60/456,641, filed on Mar. 21, 2003.

(51) Int. Cl.
*C12Q 1/68* (2006.01)

(52) U.S. Cl. .......................................................... 435/6

(58) Field of Classification Search ..................... None
See application file for complete search history.

(56) References Cited

U.S. PATENT DOCUMENTS 5,677,436 A * 10/1997 Desai et al. ................. 536/4.1

OTHER PUBLICATIONS

Zhan et al., "Replicating DNA Differently," Current Organic Chemistry, Aug. 2001, vol. 5, lines 885-902.*
Goodwin et al., "Template-Directed Synthesis: Use of a Reversible Reaction," Journal of the American Chemical Society, 1992, vol. 114, pp. 9197-9198.*
DNA-Catalyzed Polymerization Li et al.; Journal of American Chemical Society, Feb. 2002., vol. 124, No. 5, pp. 746-747.
Polymerization on Solid Supports, Li et al.; 2002, Angew Chem, vol. 114, No. 23.

* cited by examiner

*Primary Examiner*—Young J. Kim
(74) *Attorney, Agent, or Firm*—Thomas, Kayden, Horstemeyer & Risley, LLP

(57) ABSTRACT

Template-directed processes for synthesizing polymers are presented in which a sequence-specific polymer is generated from a corresponding sequence-specific template. The generated polymer has a chain length that corresponds to the chain length of the template.

7 Claims, 18 Drawing Sheets

TEMPLATE-DRIVE PROCESSES FOR SYNTHESIZING POLYMERS AND COMPONENTS RELATED TO SUCH PROCESSES

CROSS REFERENCE TO RELATED APPLICATIONS

This application claims the benefit of U.S. provisional patent applications having Ser. No. 60/366,870, filed on Mar. 22, 2002, Ser. No. 60/420,533, filed on Oct. 23, 2002, and Ser. No. 60/456,641, filed on Mar. 21, 2003, which are incorporated herein by reference in their entireties.

FIELD OF INVENTION

The present invention relates generally to polymers and, more particularly, to template-driven processes for synthesizing polymers.

BACKGROUND

In typical biological systems, polymerization reactions are driven along a template using a catalyst to specifically read sequence-specific and chain-length-specific information. Typically, the set of structural components that is involved in these in vivo reactions is limited to various combinations using only four base pairs. Additionally, the resulting polymers are typically limited to structures having phosphate-based backbones. Despite these limitations, biological polymers have been able to assemble into phenomenal structures with sophisticated architectures and intricate functions.

An ability to expand the set of structural components would provide almost limitless possibilities for new structures and properties of materials.

SUMMARY

The present disclosure provides template-directed processes for synthesizing polymers and components related to template-directed processes in biology, but greatly extending their structures and the reaction scope.

In the disclosed embodiments, the template itself acts as the catalyst for driving the reaction. The template has several binding sites that each has a particular affinity to one of the components that will bind to that site. Given this affinity, the binding energy between the template and the particular component results in an arrangement of components along the template in such a manner that a complementary structure is established along the template. If each of the components is configured to react with its adjacent components to form chemical bonds between adjacent components, then these bonds impart a stability to the complementary structure. This type of reaction preserves both sequence specificity and chain-length specificity in the complementary structure.

Other components, methods, features, and advantages will be or become apparent to one with skill in the art upon examination of the following drawings and detailed description. It is intended that all such additional components, methods, features, and advantages be included within this description.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION OF THE PREFERRED EMBODIMENTS

Figure 1A:
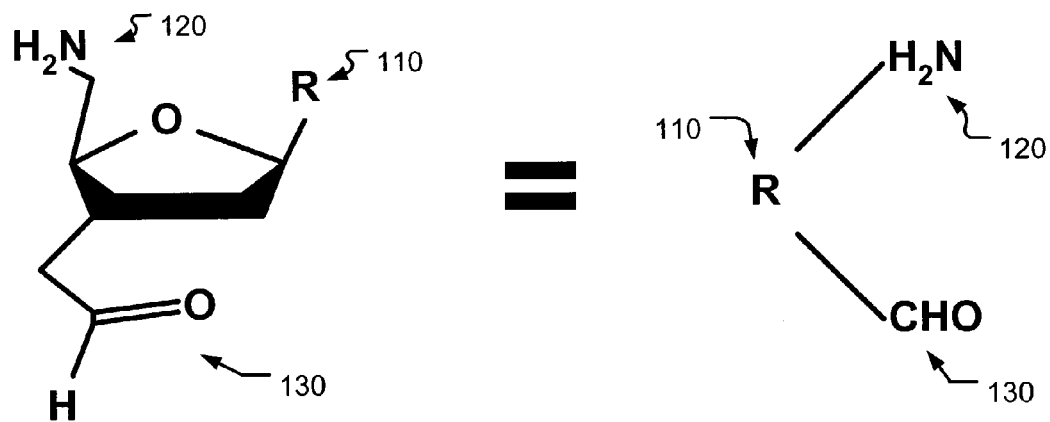
FIGS. 1A through 1E are diagrams showing embodiments of monomers that may be used in polymerization reactions to generate polymers.
Figure 1B:
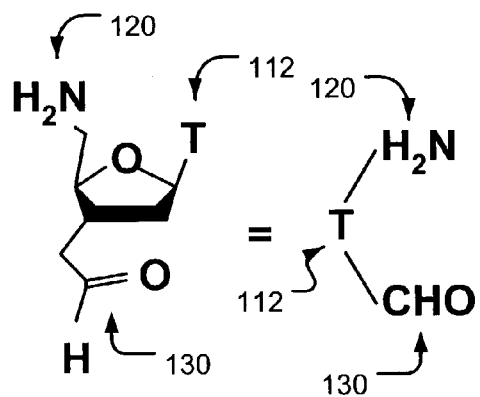
Figure 1C:
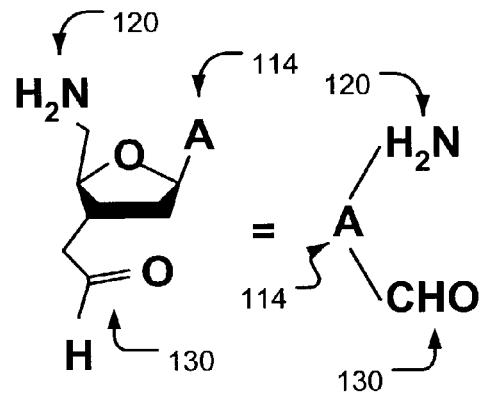
Figure 1D:
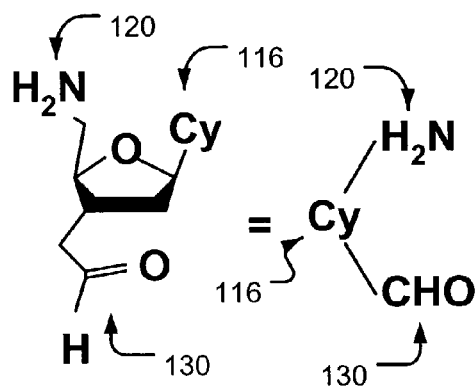

Reference is now made in detail to the description of the embodiments as illustrated in the drawings. While several embodiments are described in connection with these drawings, there is no intent to limit the invention to the embodiment or embodiments disclosed herein. On the contrary, the intent is to cover all alternatives, modifications, and equivalents.

FIGS. 1A through 9 show several embodiments in which template-directed processes, and components related to such processes, are shown. In those embodiments, the template itself acts as the catalyst for driving the reaction. The template has several binding sites that each has a particular affinity to one of the components that will bind to that site. Given this affinity, when a component (e.g., monomer, oligomer, etc.) binds to its corresponding binding site on the template, the binding energy between the template and that component results in an organizing of the components along the template in such a manner that a complementary structure is established along the template. If each of the components is configured to react with its adjacent components to form chemical bonds between adjacent components, then these bonds impart a further stability to the complementary structure. As one can see, this type of reaction preserves both a sequence specificity and a chain-length specificity in the complementary pair. Also, this type of reaction uses the template itself to determine the organization of the complementary structure.

FIGS. 1A through 1E are diagrams showing embodiments of monomers that may be used in a polymerization reactions to generate polymers. As shown in FIG. 1A, an example embodiment of a monomer is a modified nucleoside with two reactive ends: one reactive end having an amine ($H_2N$) 120 chemically bonded to the 5'-carbon, and the other reactive end having an acetaldehyde ($CH_2CHO$) 130 chemically bonded to the 3'-carbon. In other words, for the modified nucleoside, the hydroxyl group that normally appears on the 5'-carbon of a typical nucleoside is replaced by an amine 120, and the hydroxyl group that normally appears on the 3'-carbon of a typical nucleoside is replaced by an acetaldehyde 130. Thus, two reactive ends are created on the modified nucleoside by placing an amine 120 and an acetaldehyde 130 on the 5'-carbon and the 3'-carbon, respectively. Since, in aqueous solution, amines readily react with acetaldehydes to form imines, when the amine 120 of one monomer and the acetaldehyde 130 of another monomer are arranged in close proximity to each other, the resulting reaction forms an imine (not shown) that chemically bonds the two monomers. The imine is converted to an amine (not shown) in the presence of a reducing agent. Examples of such reactions are provided with reference to FIGS. 4A through 6C.

Figure 1E:
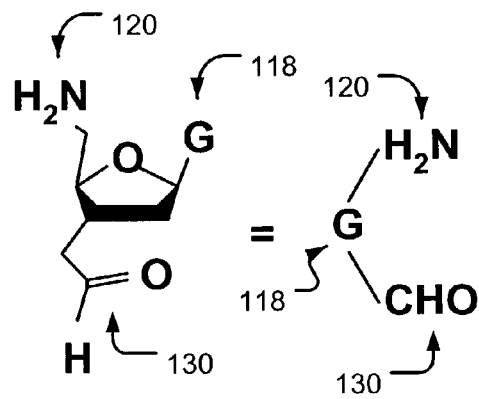

As shown in FIGS. 1B through 1E, the modified nucleoside may be, at a minimum, a modified thymidine (FIG. 1B), a modified adenosine (FIG. 1C), a modified cytidine (FIG. 1D), a modified guanosine (FIG. 1E). While not shown here, the modified nucleoside may also be a modified uridine, a modified inosine, or possibly any nucleoside or structure having an alternative complementary-associating partner or complementary-pairing partner. While the modified cytidine nucleoside is denoted with "Cy" to distinguish between the symbol for carbon, "C," it should be appreciated that, in conventional nomenclature, the cytidine would be denoted with "C." Since each of the modified nucleosides has an amine 120 as one reactive end and an acetaldehyde 130 as another reactive end, two modified nucleosides may readily react with each other in aqueous solution.

Figure 2A:
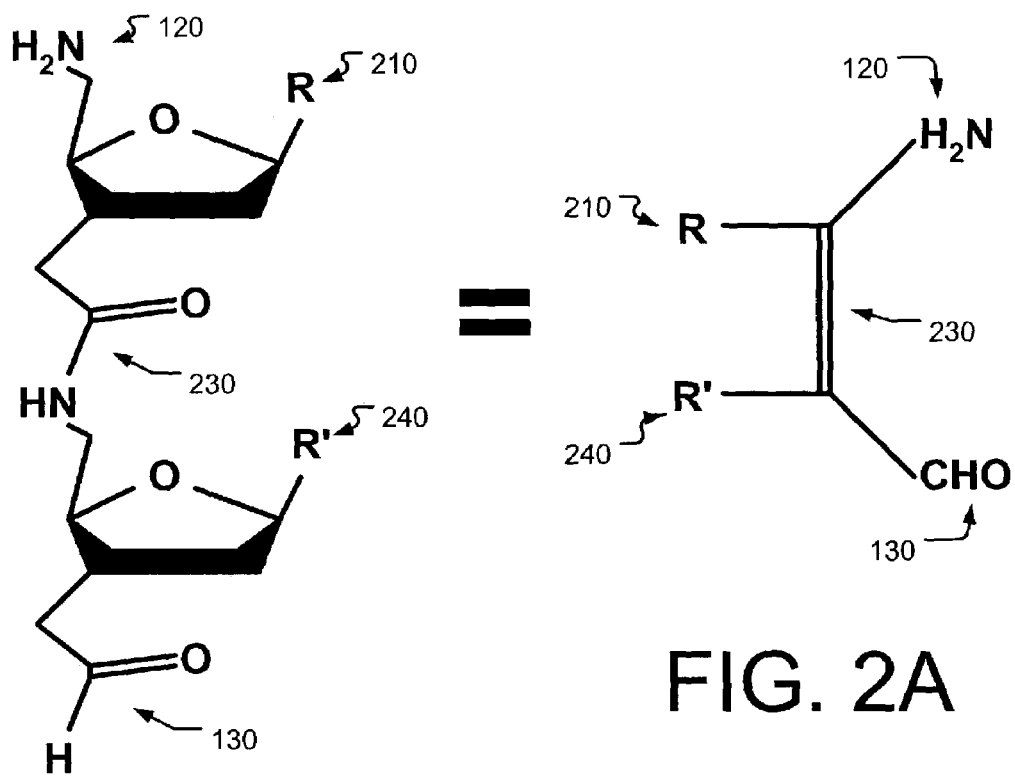
FIGS. 2A and 2B are diagrams showing embodiments of oligomers that may be used in polymerization reactions to generate polymers.
Figure 2B:
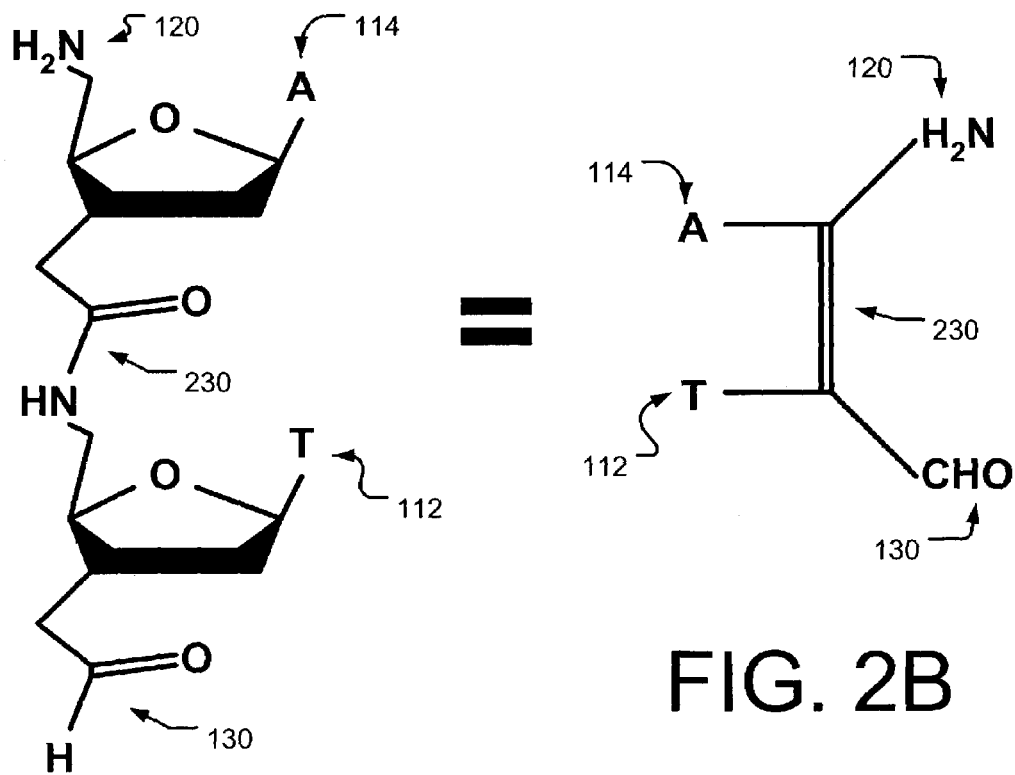

FIGS. 2A and 2B are diagrams showing embodiments of oligomers that may be used in polymerization reactions to generate polymers. As shown in FIG. 2A, one embodiment of an oligomer is a dimer comprising two nucleosides chemically bonded to each other by an amide (NCO) 230. More specifically, the amide carbonyl 230 is derived from the aldehyde carbonyl of the first modified nucleoside in the dimer, and the amide amine is derived from the second modified nucleoside in the dimer. Thus, the oligomer has two reactive ends: one reactive end defined by the amine 120 on the 5'-carbon of the first modified nucleoside, and the other reactive end defined by the acetaldehyde 130 on the 3'-carbon of the second modified nucleoside.

Since, in aqueous solution, amines readily react with acetaldehydes to form imines, when the amine 120 of one oligomer and the acetaldehyde 130 of another oligomer are arranged in close proximity to each other, the resulting reaction forms an imine (not shown) that chemically bonds the two monomers. The imine is converted to an amine (not shown) in the presence of a reducing agent. Examples of such reactions are provided with reference to FIGS. 4A through 6C.

As shown in FIG. 2B, in one embodiment, the first monomer is a modified adenosine (A) 114 nucleoside having the amine 120 at the 5'-carbon and the amide 230 connected to the second monomer that is a modified thymidine (T) 112. The 2nd nucleoside maintains the acetaldehyde 130 at the 3'-end. However, it should be appreciated that the oligomer of FIG. 2B may comprise other monomer units such as those shown in FIGS. 1B through 1E. In this regard, the first monomer in the dimer of FIG. 2B may be a modified thymidine, a modified adenosine, a modified cytidine, a modified guanosine, a modified uridine, a modified inosine, etc. Similarly, the second monomer in the dimer of FIG. 2B may be a modified thymidine, a modified adenosine, a modified cytidine, a modified guanosine, a modified uridine, a modified inosine, etc.

While dimers are shown in FIGS. 2A and 2B, it should be appreciated that the oligomer may be a trimer, a tetramer, a pentamer, a hexamer, a heptamer, an octamer, or any other oligomer, as long as the oligomer has two reactive ends (e.g., an amine 120 at one end and an acetaldehyde 130 at the other end).

Figure 3:
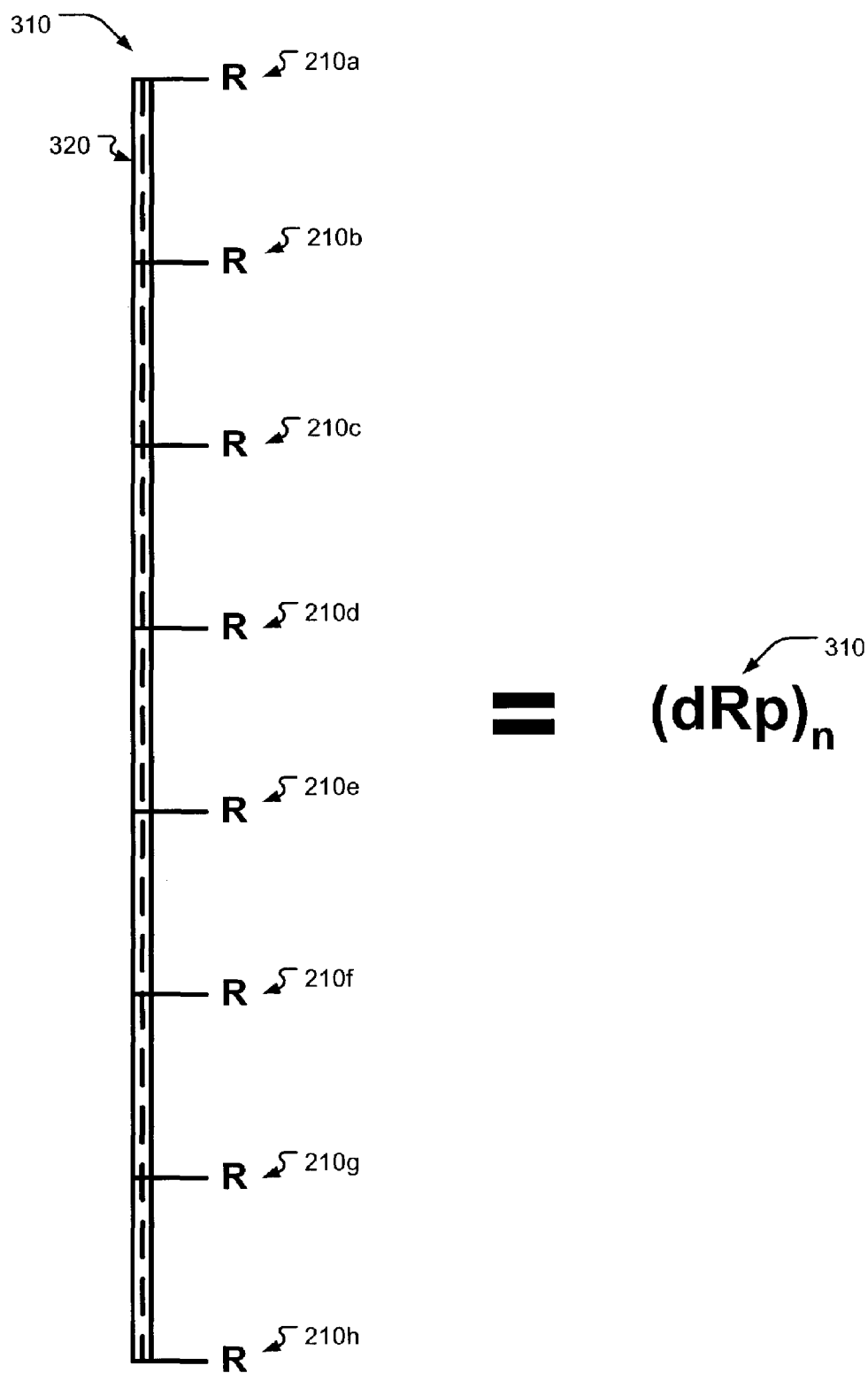
FIG. 3 is a diagram showing an embodiment of a template used to direct a polymerization process.

FIG. 3 is a diagram showing an embodiment of a template 310 used to direct a polymerization process. Specifically, the embodiment of FIG. 3 shows a single-strand deoxyribonucleic acid (DNA) octamer as the template 310. The DNA octamer 310 has eight nucleotide (R) monomers $210a \ldots 210h$ (collectively referred to as 210) that are connected by a phosphate backbone 320. It should be appreciated that the nucleotides 210 in the single-strand DNA may have a conventional purine (e.g., adenine or guanine), a conventional pyrimidine (e.g., cytosine, thymine, or uracil), or an alternative base pair. One example of a specific template is shown in the paper "DNA Catalyzed Polymerization," by Li et al., which is fully set forth in U.S. provisional patent application having Ser. No. 60/366,870, filed on Mar. 22, 2002, and "Polymerization on Solid Supports," by Li et al., which is fully set forth in U.S. provisional patent application having Ser. No. 60/420,533, filed on Oct. 23, 2002. While primarily homopolymers are shown in the papers "DNA Catalyzed Polymerization" and "Polymerization on Solid Supports," it should be appreciated that heteropolymers may also be used for the template. For simplicity, the template is referred to herein as $(dRp)_n$, where the "R" represents the base pair, and "n" represents the number of monomers in the template. Thus, an eight-unit oligodeoxyadenosine template would be represented as $(dAp)_8$, an eight-unit oligodeoxycytidine template would be represented as $(dCp)_8$, etc.

By arranging nucleotides in a specific sequence, the template of FIG. 3 may be used to direct polymerization reactions that produce chain-length-specific and sequence-specific polymers. In other words, by providing a specific sequence of nucleotides on the template, a complementary sequence may be generated by directing polymerization along the sequence-specific, chain-length-specific template. Examples of template-directed polymerization reactions are provided in FIGS. 4A through 6C.

Figure 4A:
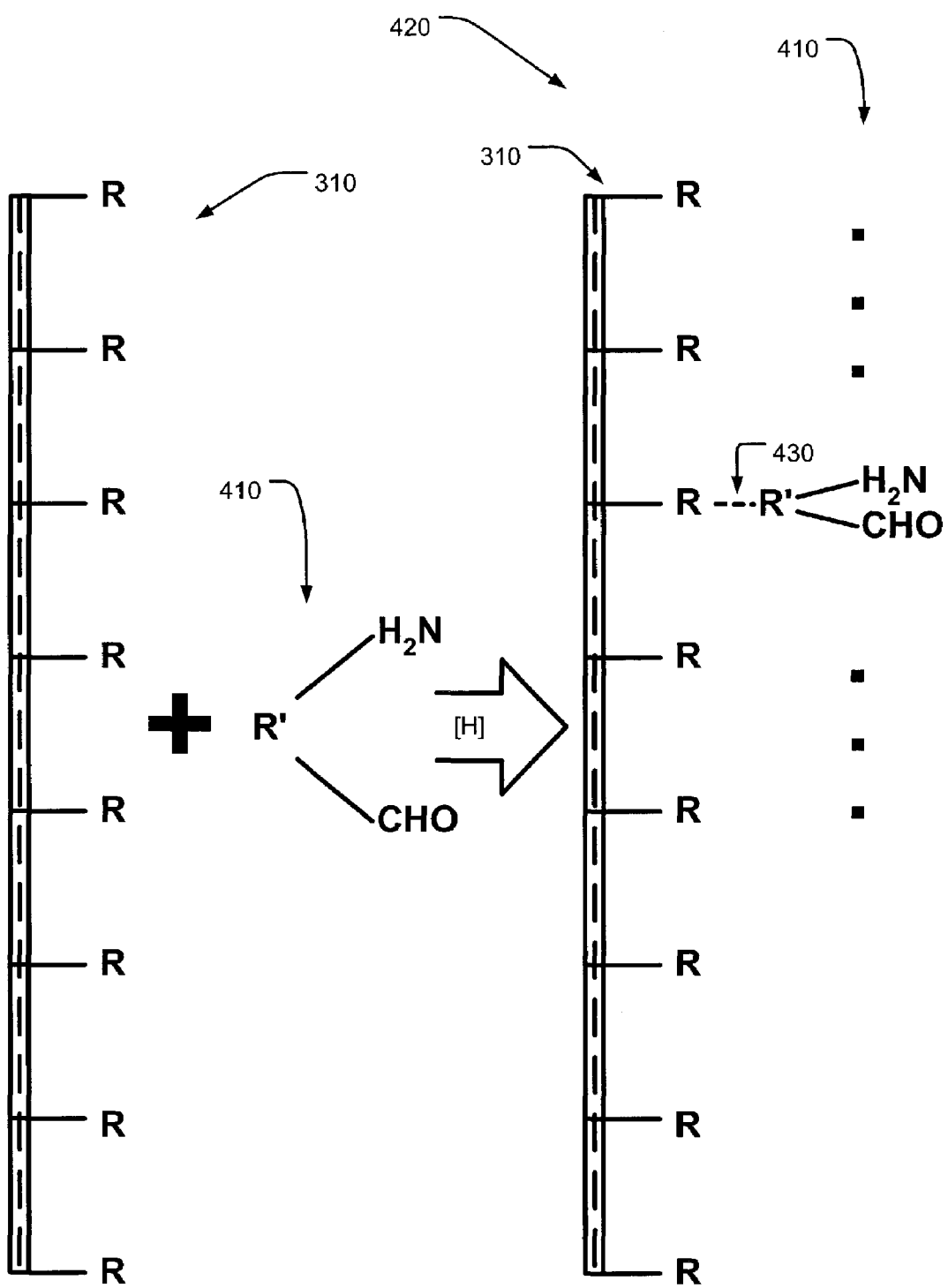
FIGS. 4A through 4E are diagrams showing an embodiment of a polymerization reaction.
Figure 4B:
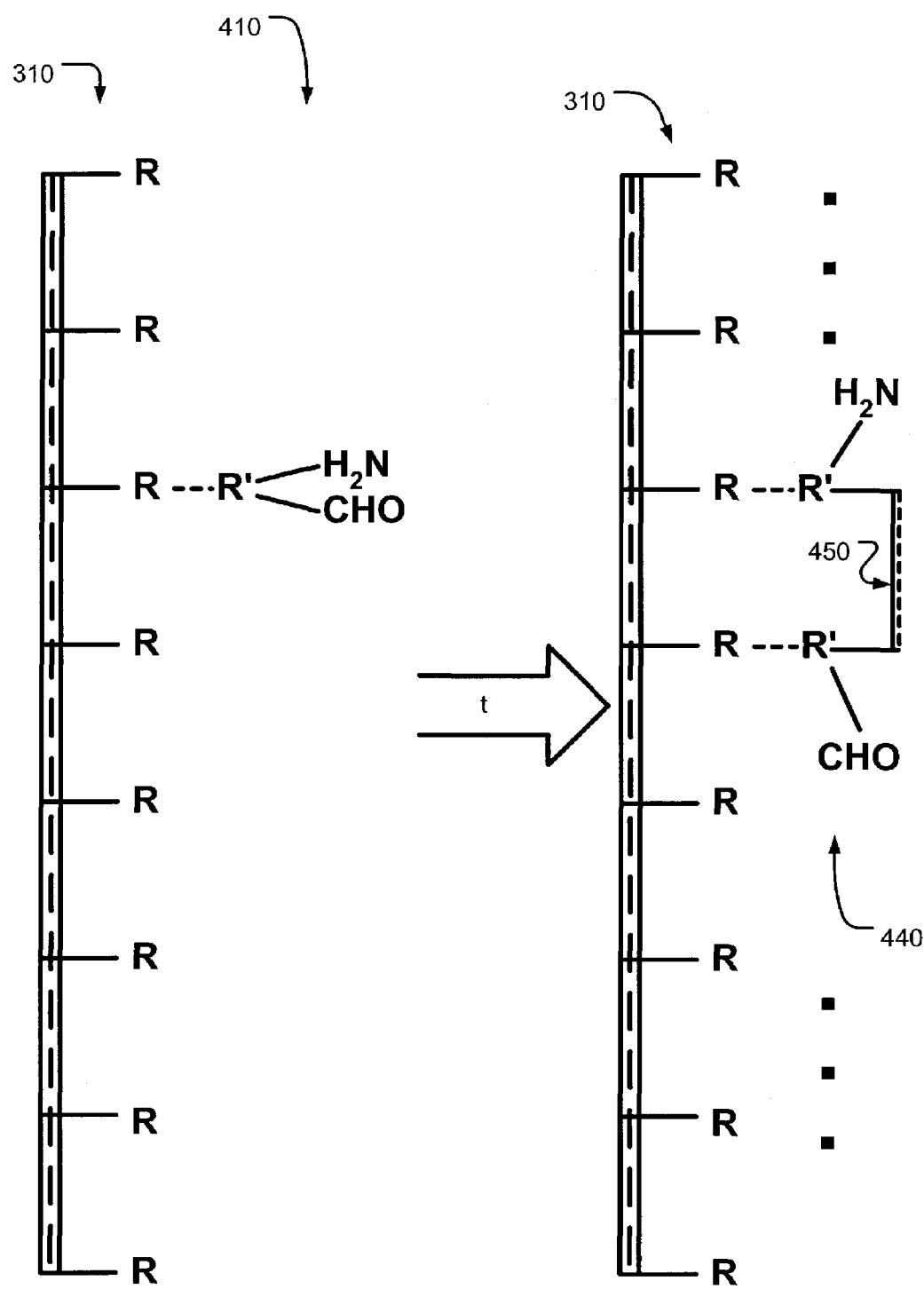

FIGS. 4A through 4E are diagrams showing an embodiment of a polymerization reaction. As shown in FIG. 4A, a $(dRp)_8$ DNA homopolymer template 310 is used to preorganize R' monomers 410 for imine formation. The R' monomers arrange themselves on the template due to the attraction between the R binding sites of the template 310 and the R' binding site on each of the R' monomers 410. With an n-unit template, there are n–1 binding sites that contribute in an antiparallel associating equilibrium (see FIG. 4B). The rate of reaction, and irreversible monomer-monomer ligation, is a function of this imine concentration. This appears to enable all the monomers to react to give amine dimers before any of the dimers react.

Figure 4C:
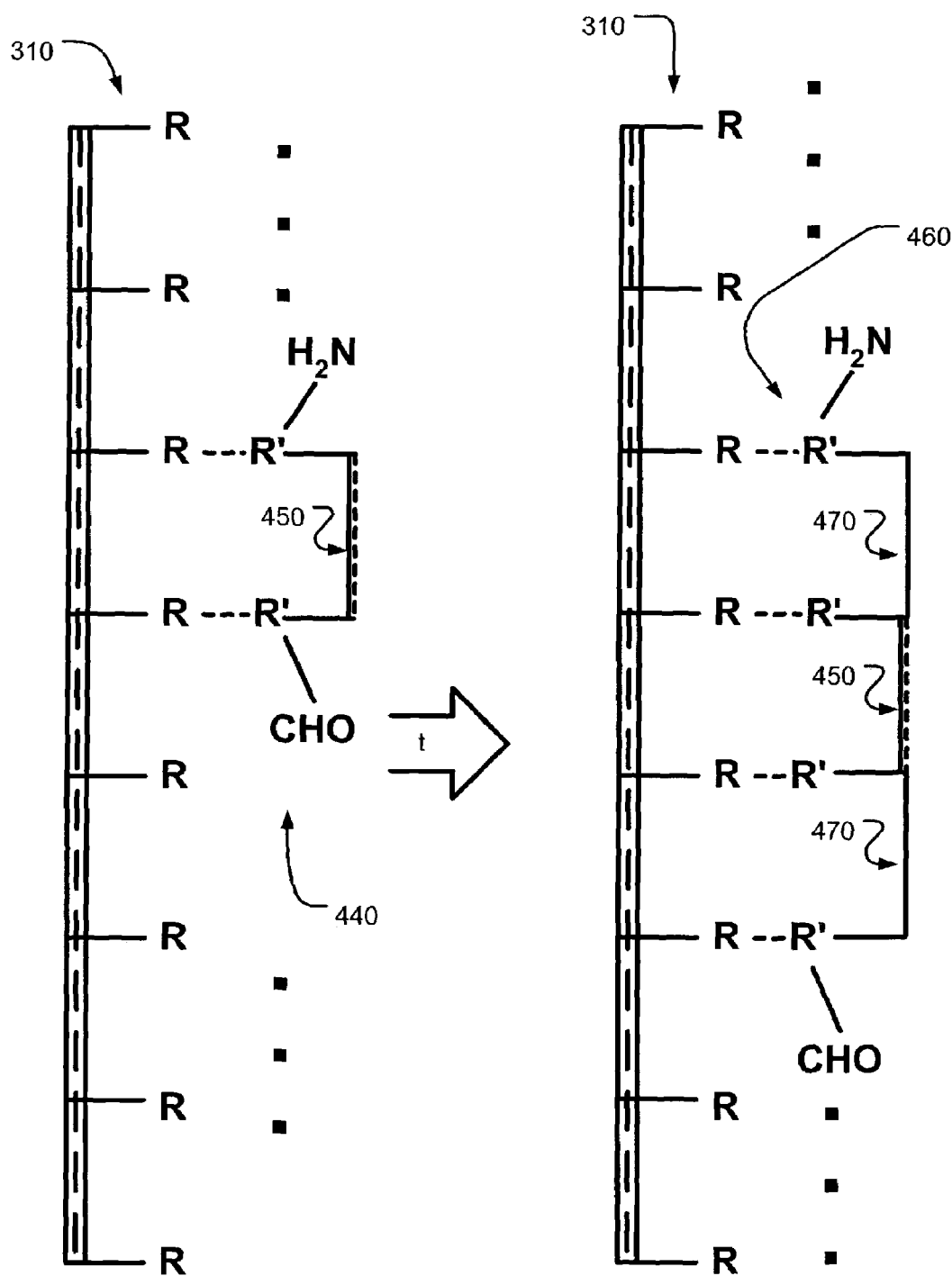
Figure 4D:
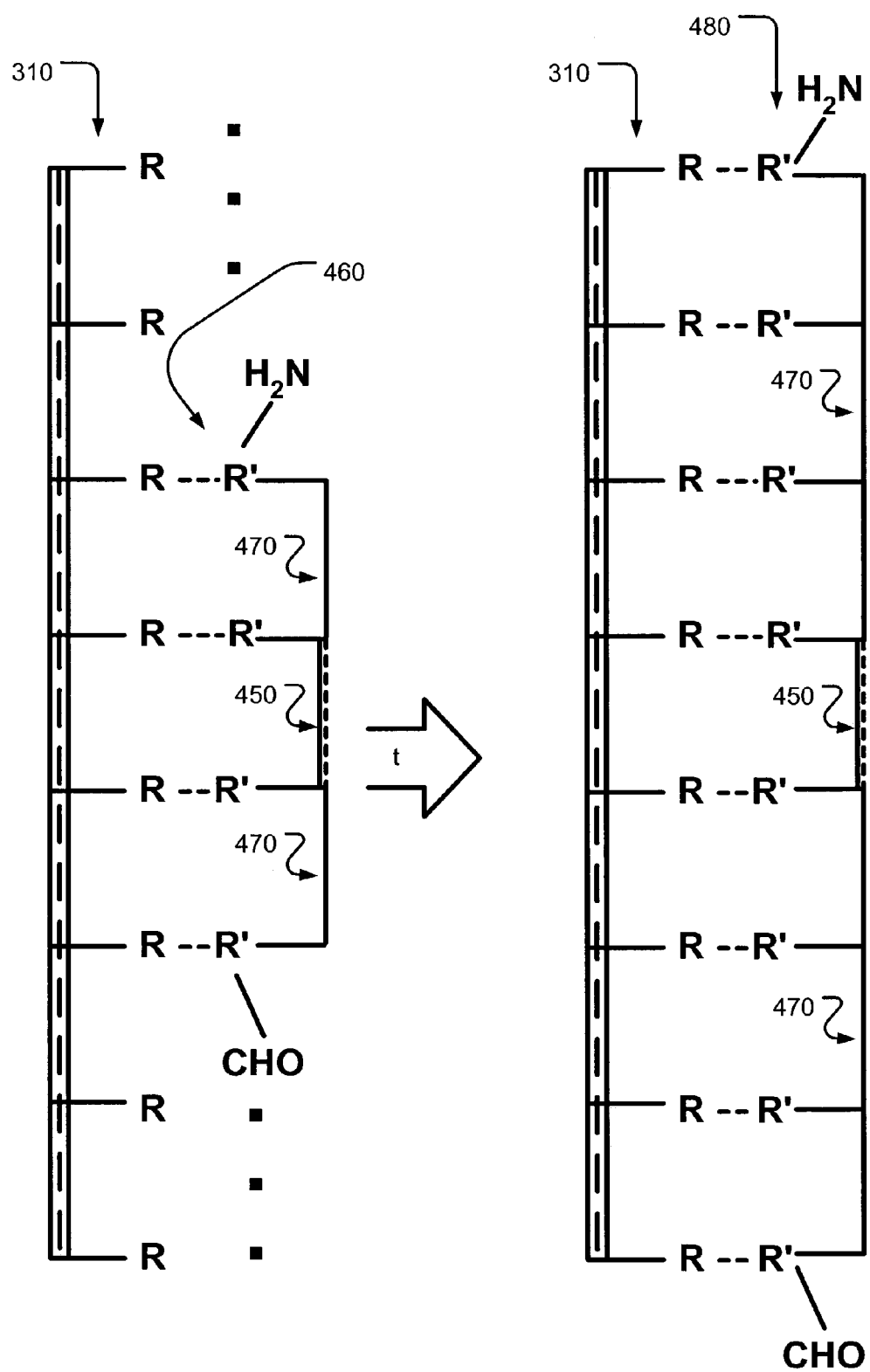
Figure 4E:
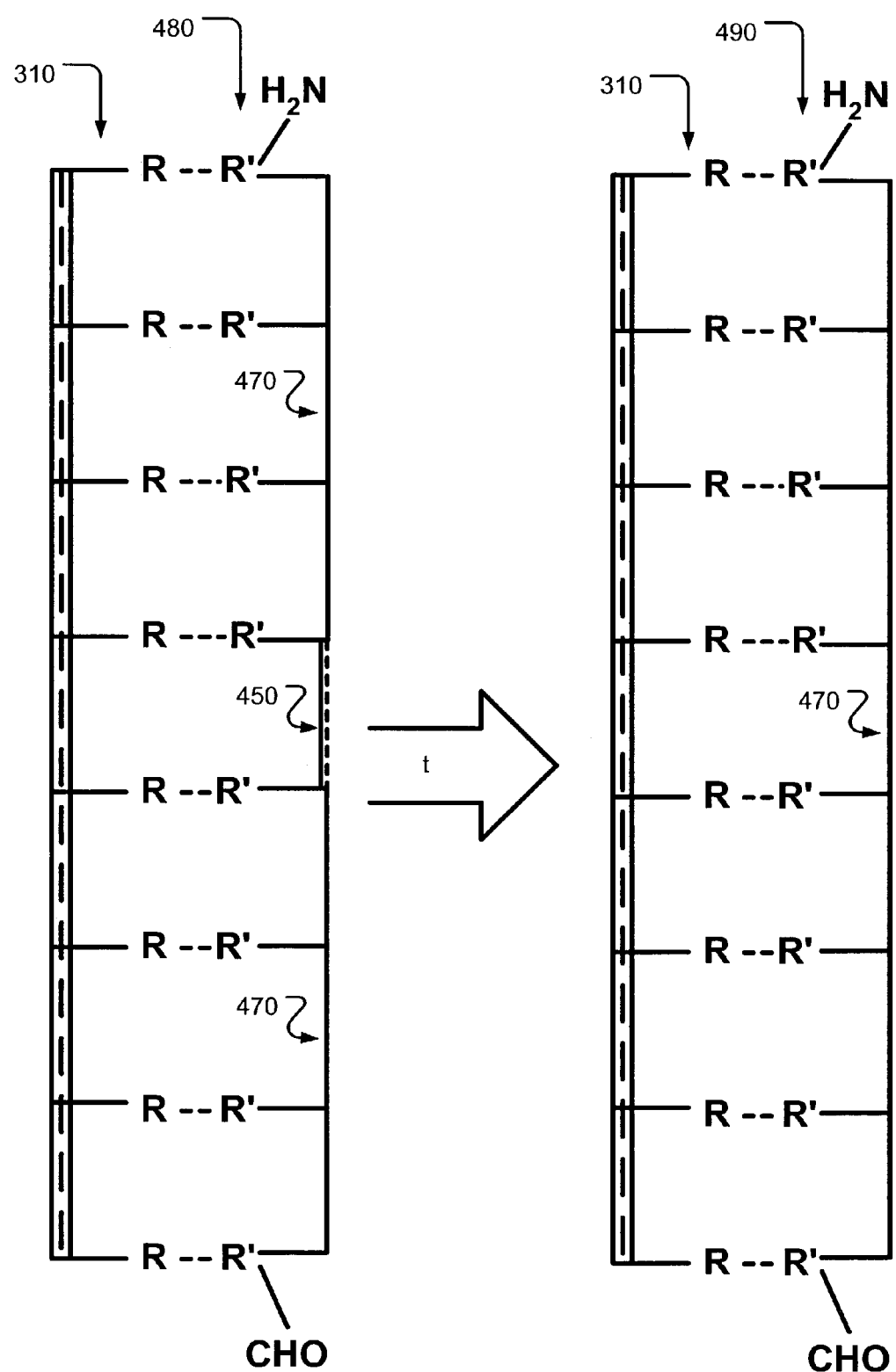

As shown in FIG. 4C and the paper "DNA Catalyzed Polymerization," the resulting dimers 460 then associate on the template, but with only n–3 total binding sites. Still the dimers react faster than the product tetramers 480 so that overall the reaction shows essentially clean exponential growth kinetics. The reaction further progresses from tetramers 480 to octamers 490, as shown in FIG. 4E through the reduction reaction of the intermediate imine 450 to an amine 470.

As shown in FIGS. 4A through 4E and the paper "DNA Catalyzed Polymerization," the reaction shows exponential growth in product molecular weight. In this regard, when monomers are used as the basis units, the polymerization process proceeds to dimers, then tetramers, then octamers, then 16-mers, etc., depending on the length of the template. Also, as shown in the paper "DNA Catalyzed Polymerization," due to the increased concentration of amine/acetaldehyde pairs for the monomers, the monomers displayed a higher imine concentration during the initial reaction step than the dimers, the dimers displayed a higher imine concentration than the tetramers, etc. From FIGS. 4A through 4E, it can be seen that, for relatively long chain-length sequences, this step-growth process may provide greater efficiency than chain-growth kinetics in which the chain is sequentially grown one monomer at a time.

Figure 4F:
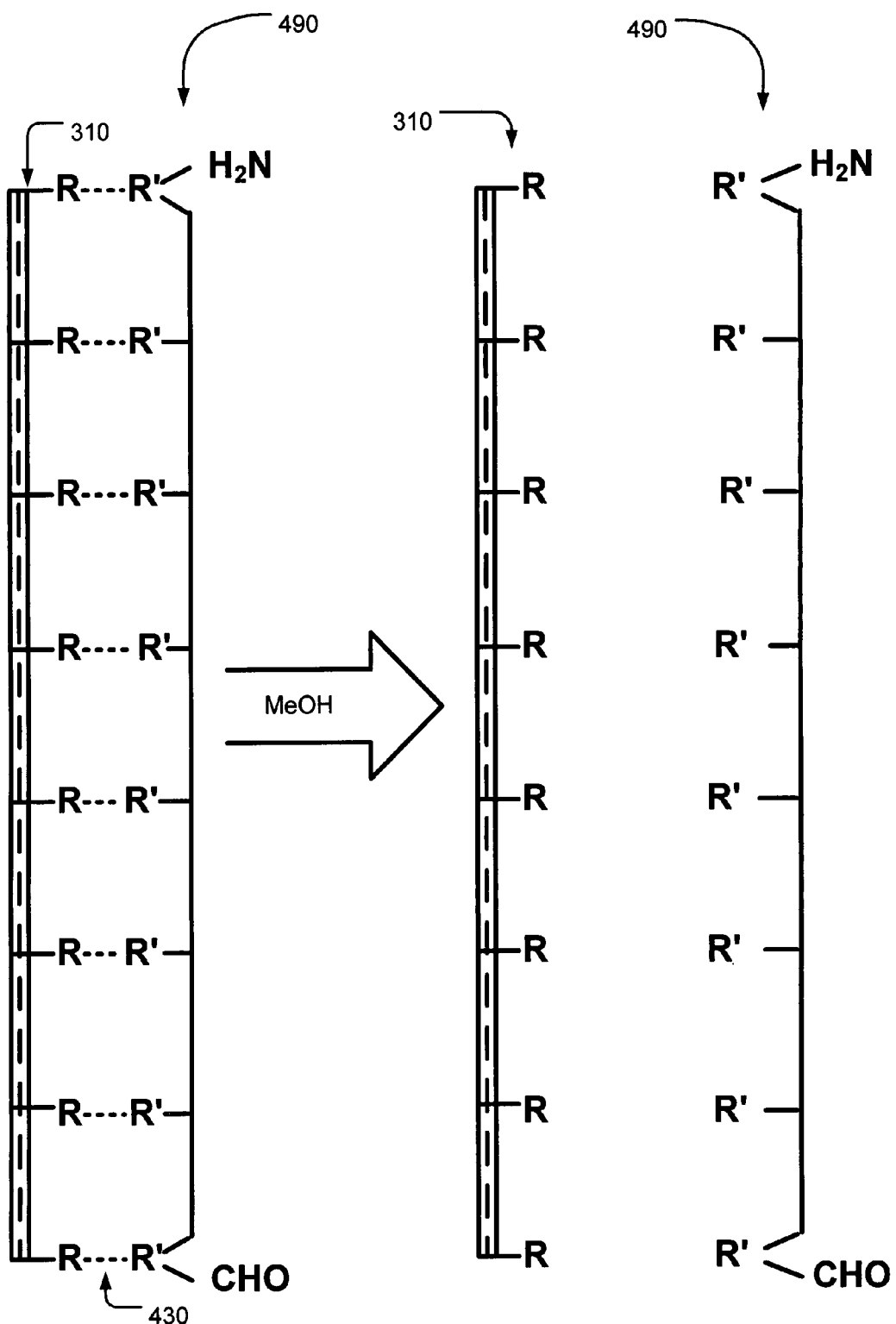
FIG. 4F is a diagram showing an embodiment of a process to recover the generated polymer.

If the $(dRp)_8$ template is placed on a solid support (e.g., plystyrene/polyethyleneglycol copolymer support beads, etc.), as shown in FIG. 4F and the paper "Polymerization on Solid Supports," the generated R' polymer 490 may be recovered using specific elution techniques (e.g., a hot methanol (MeOH) elution). Additionally, since the resulting backbone of the generated complementary strand associated tightly to the template backbone, other elution conditions may be used to remove unused reactants from the reaction mixture.

The process outlined in FIGS. 4A through 4F may also be repeated to produce multiple polymers that are both sequence-specific and chain-length-specific. Since the placement of polymers on solid supports is known in the art, other types of solid supports should be appreciated by those having skill in the art.

Figure 5A:
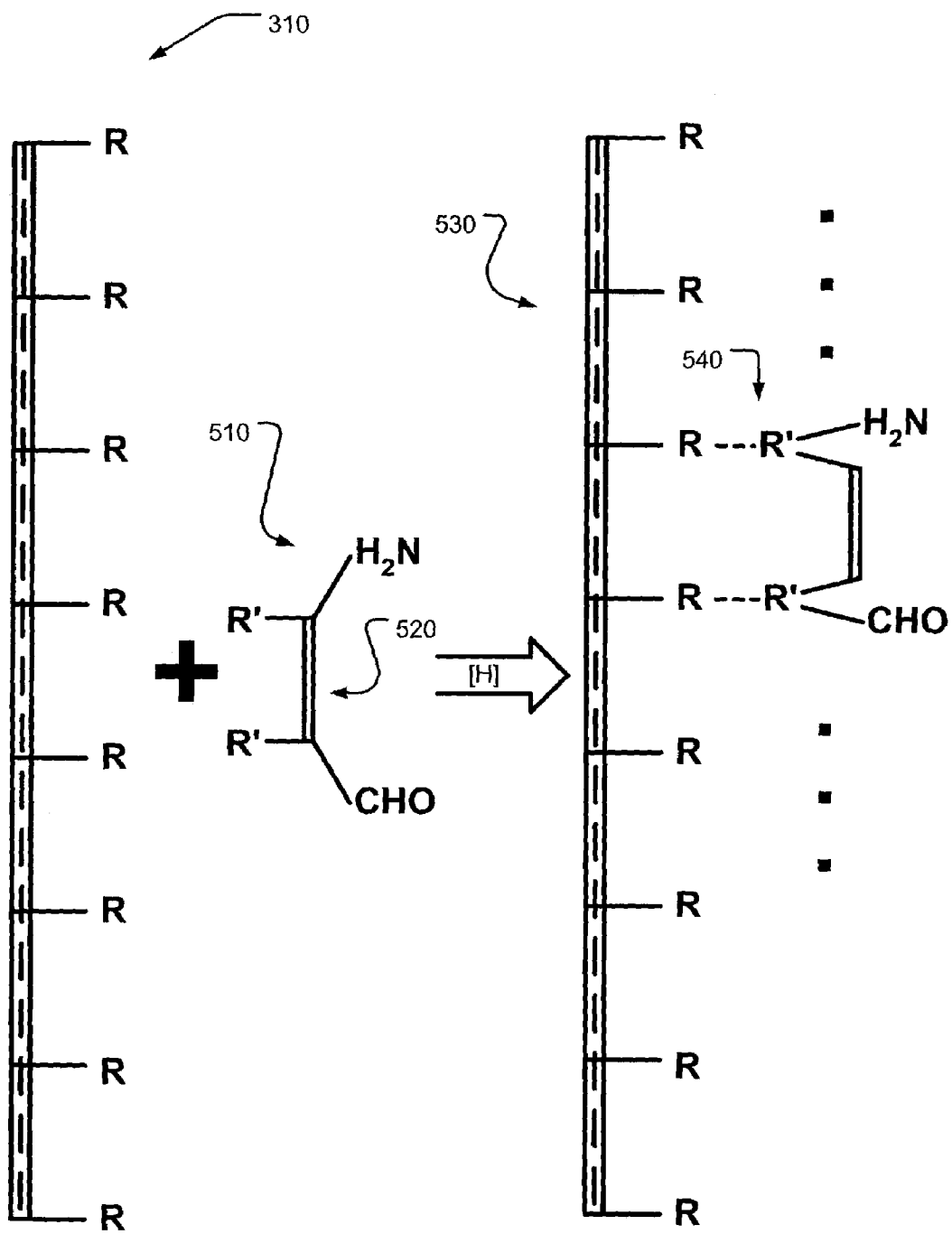
FIGS. 5A through 5D are diagrams showing another embodiment of a polymerization reaction.

FIGS. 5A through 5D are diagrams showing another embodiment of a polymerization reaction. As shown in FIG. 5A, the $(dRp)_8$ is again used to direct the polymerization reaction. Like the process beginning with R' monomers as shown in FIG. 4A, the process of FIG. 5A begins with R' having two reactive ends:,one end having an amine and the other end having an acetaldehyde. However in this case R' is the dimers 510, having two R' monomers that are chemically bonded to each other by an amide 520 (see, e.g., FIGS. 2A and 2B).

Upon initiation of the process, the R' dimers 510 associate with the $(dRp)_8$ template at five (n–3) possible sites due to the attractive forces between the R binding sites on the template 310 and the R' residues of the dimers 510. Once the chemical bonds are formed between the R' dimers 510 and the template 310, the reaction progresses to FIG. 5B.

Figure 5B:
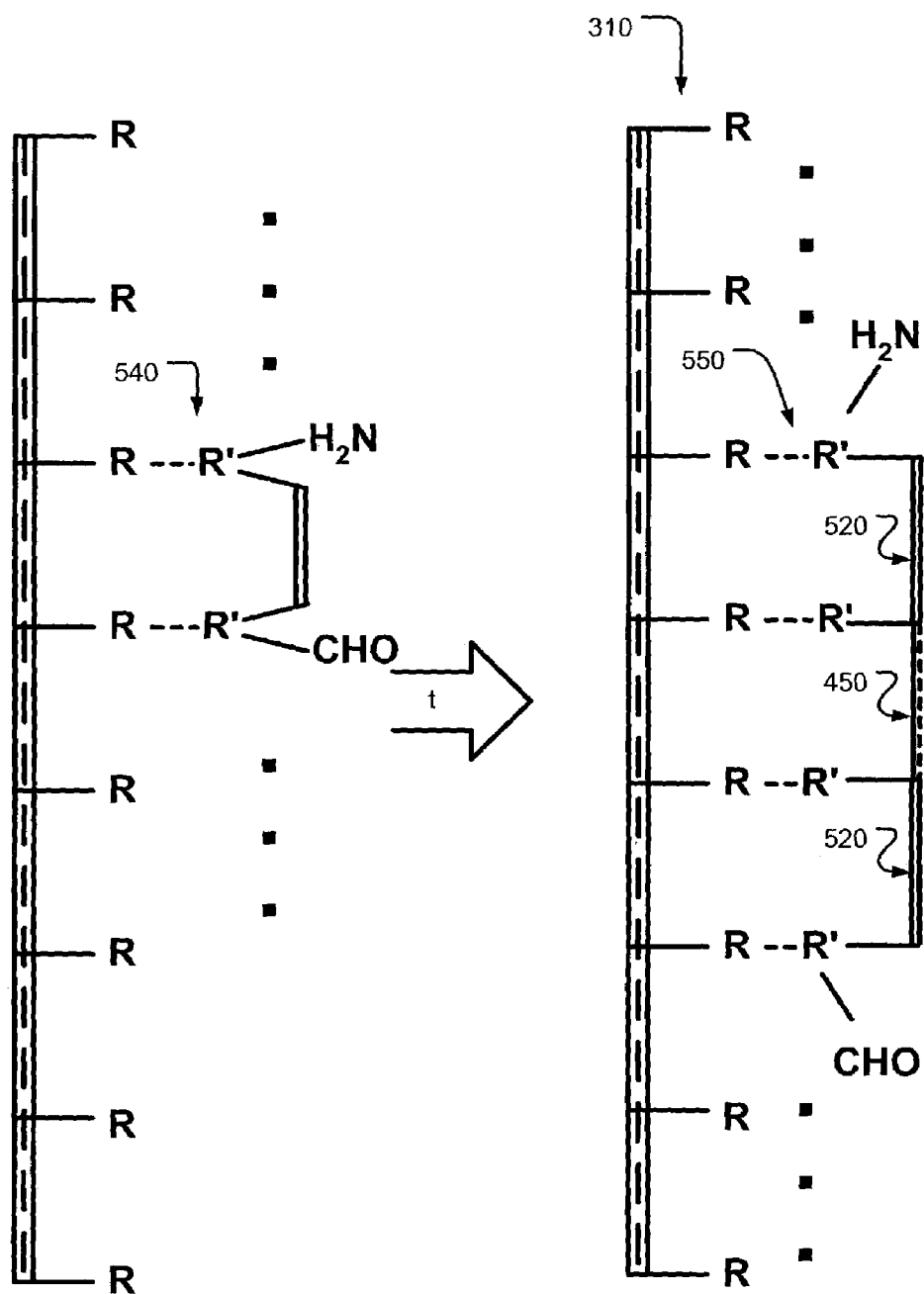
Figure 5C:
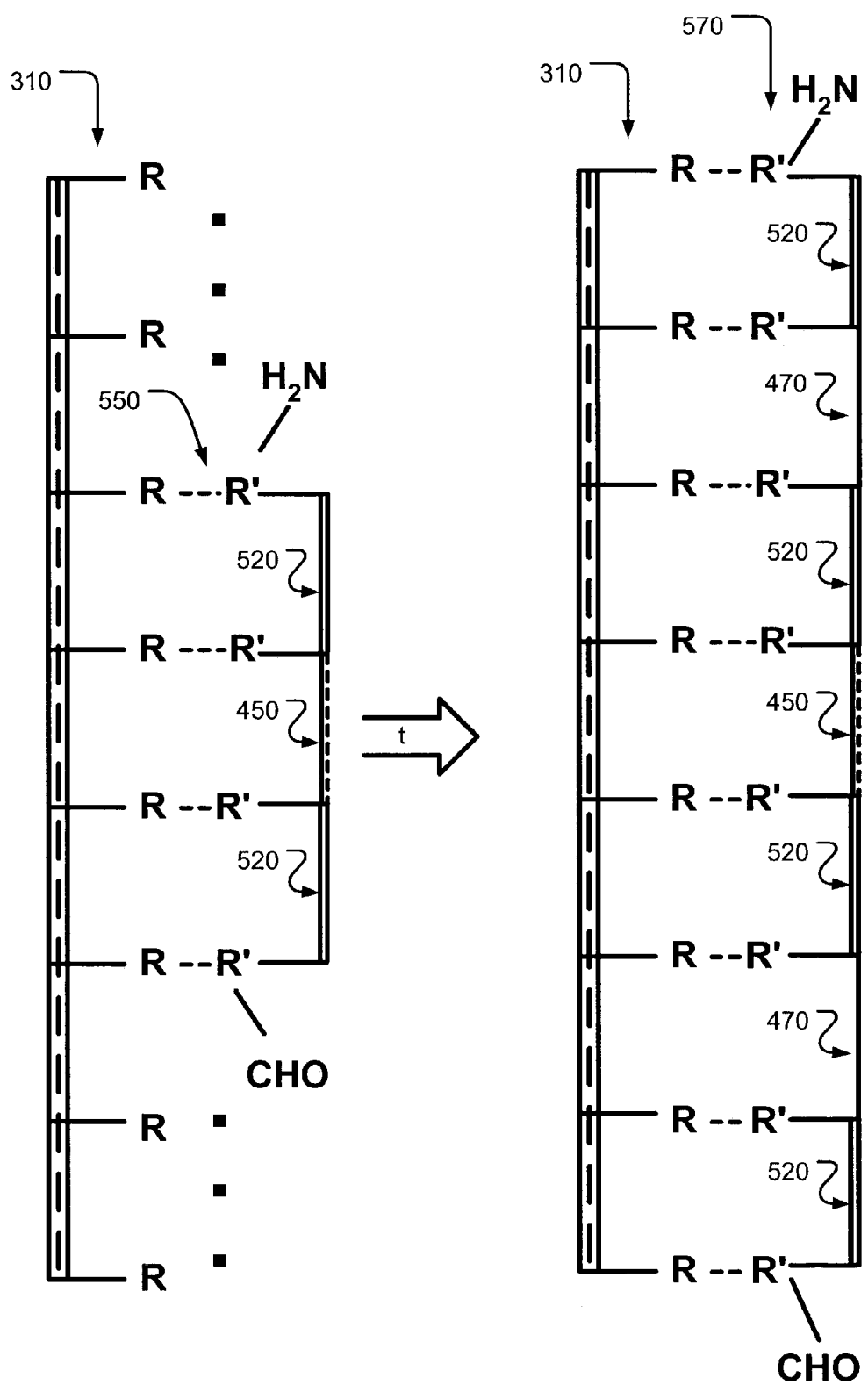

Over the course of time, as shown in FIG. 5B, the primary amines of each dimer 510 reacts with the acetaldehyde of an adjacent dimer 510, thereby further forming intermediate imines 450 between the adjacent dimers 510. The intermediate imines 450 between each alternate pair of dimers 510 are subsequently reduced, as shown in FIG. 5C, thereby forming a more stable amine 470. As shown in the paper "DNA Catalyzed Polymerization" and FIG. 5C, this results in the formation of tetramers 570, which each have alternating amines 450 and amides 520.

Continuing in FIG. 5D, intermediate imines 450 can subsequently form between pairs of tetramers 570, at only one site on the octomer template, and is further reduced to amines 470, thereby resulting in an octamer 580 with alternating amines 470 and amides 520 along its backbone.

As shown in the paper "Polymerization on Solid Supports," the generated R' polymer 580 may be recovered with a hot methanol (MeOH) elution. Thus, if the $(dRp)_8$ template is placed on a solid support, the process outlined in FIGS. 5A through 5D may be repeated to produce multiple polymers that are both sequence-specific and chain-length-specific.

Figure 6A:
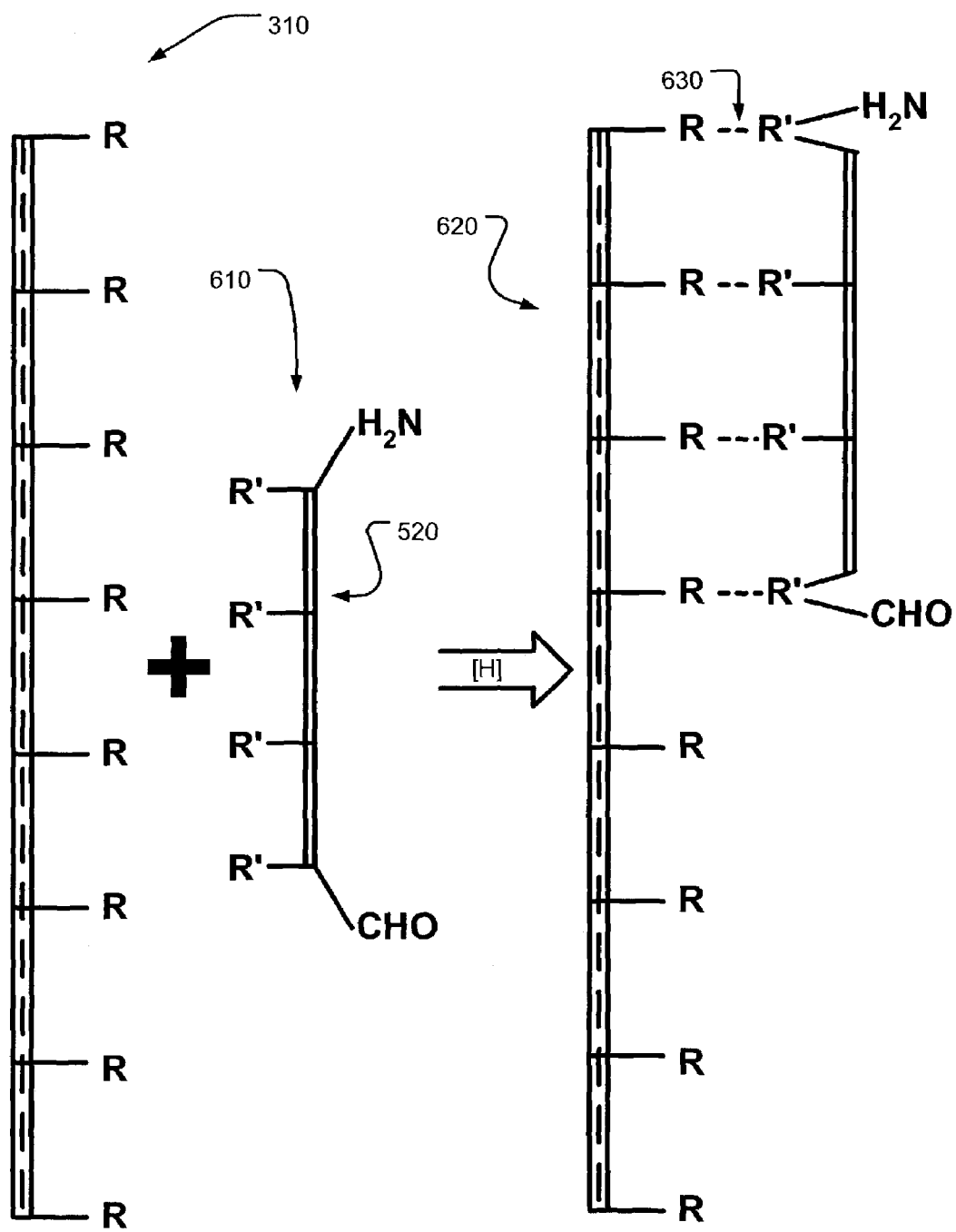
FIGS. 6A through 6C are diagrams showing yet another embodiment of a polymerization reaction.
Figure 6B:
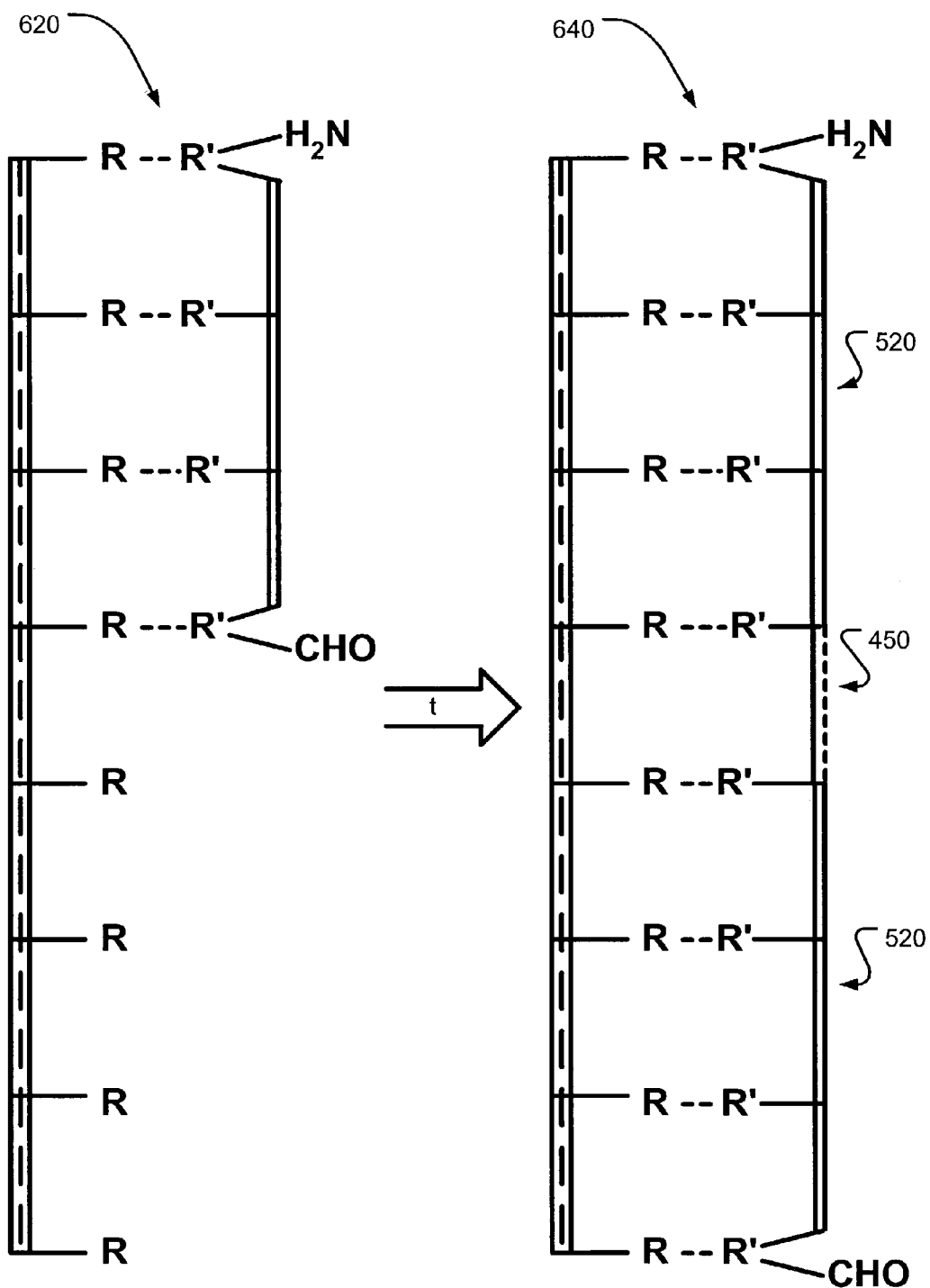
Figure 6C:
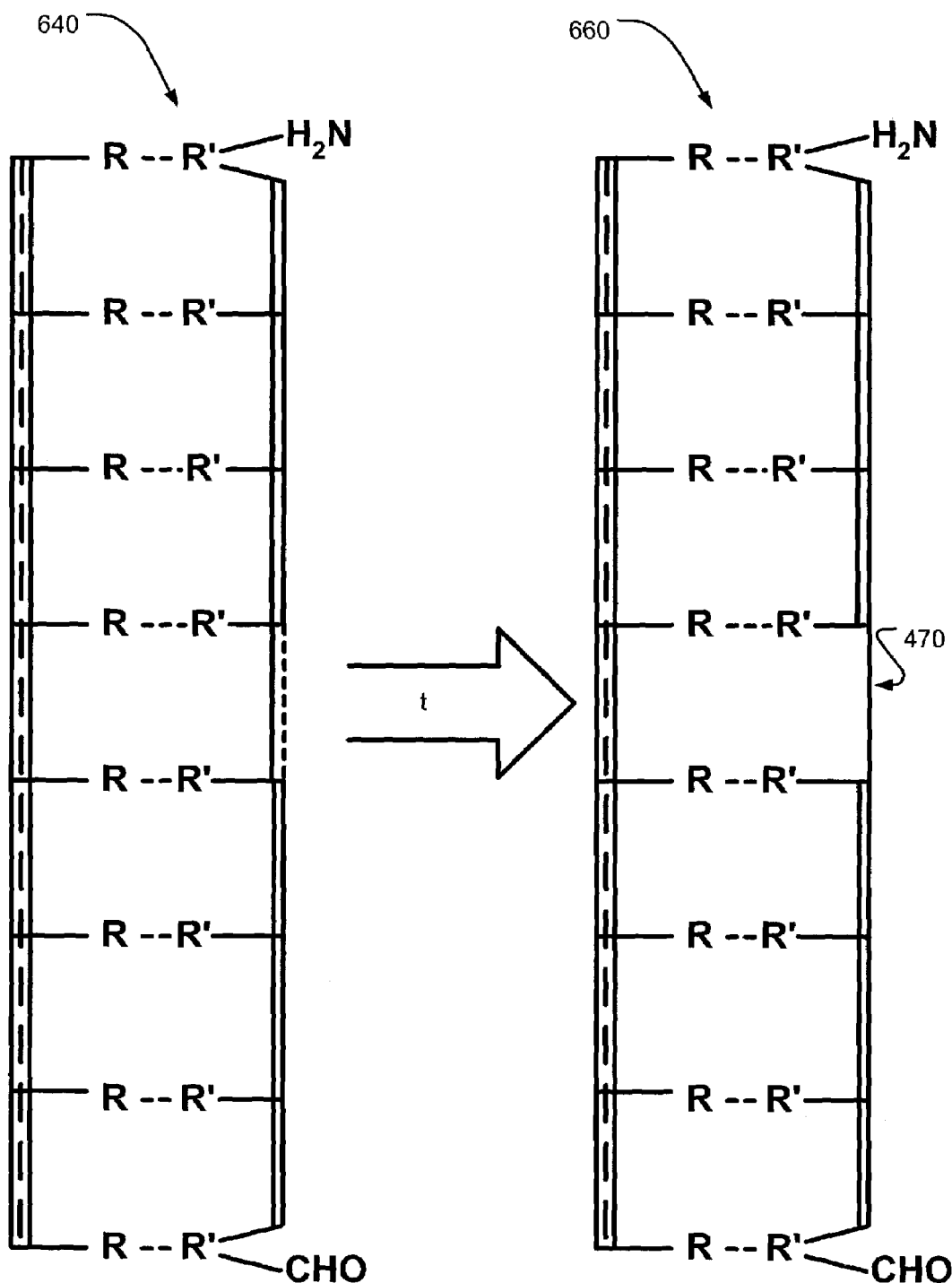

FIGS. 6A through 6C are diagrams showing yet another embodiment of a polymerization reaction that is outlined in the paper "DNA Catalyzed Polymerization." As shown in FIG. 6A, the $(dRp)_8$ is again used to direct the polymerization reaction. However, rather than beginning with R' monomers as shown in FIG. 4A, or R' dimers as shown in FIG. 5A, the process of FIG. 6A begins with R' tetramers 610 having two reactive ends: one end having an amine and the other end having an acetaldehyde. The tetramers 610 may be seen as four R' monomers that are chemically bonded by amides 520.

Upon initiation of the process, the R' tetramers 610 align along the $(dRp)_8$ template due to the attractive forces between the R binding sites on the template 310 and the R' binding sites on the tetramers 610. Once the chemical bonds are formed between the R' tetramers 610 and the template 310, the reaction progresses to FIG. 6B.

Over the course of time, as shown in FIG. 6B, the amine of one tetramer 610 reacts with the acetaldehyde of an adjacent tetramer 610, thereby forming an intermediate imine 450 between the adjacent tetramers 610. Continuing in FIG. 6C, the imine 450 is subsequently reduced to an amine 470, thereby resulting in an R' octamer having an amine 470 and amide 520 backbone.

While not shown, it should be appreciated that the generated R' polymer 660 may, again, be recovered with a hot methanol (MeOH) elution. Thus, if the $(dRp)_8$ template is placed on a solid support, then the process outlined in FIGS. 6A through 6C may be repeated to produce multiple polymers that are both sequence-specific and chain-length-specific.

Figure 5D:
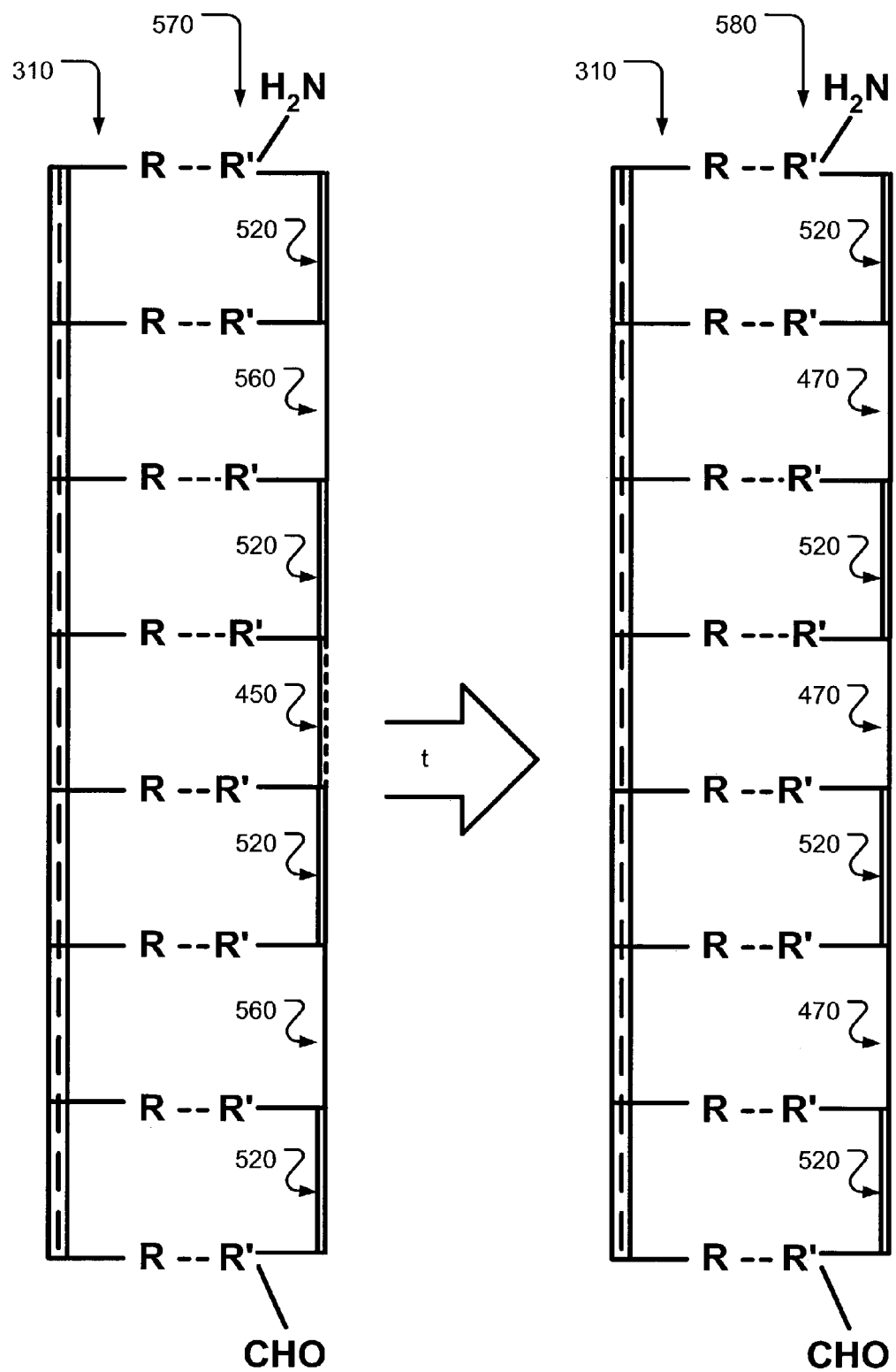
Figure 7:
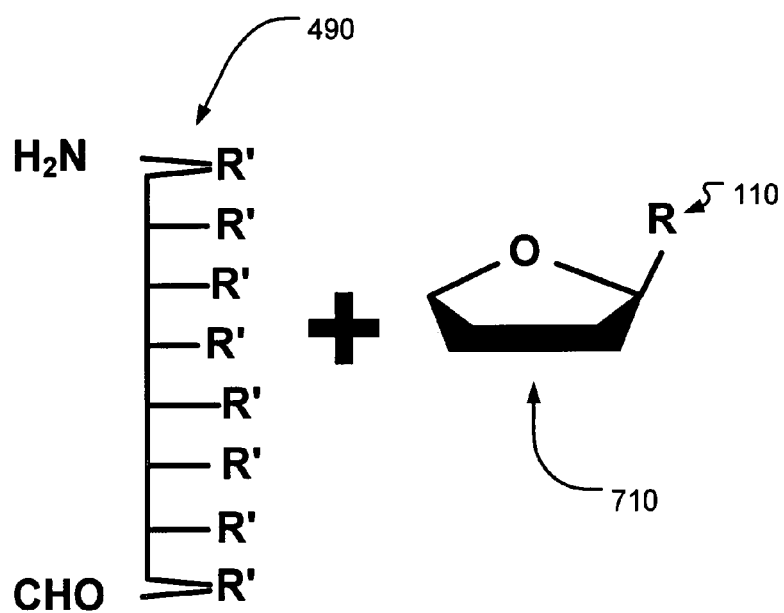
FIG. 7 is a diagram showing an embodiment of a process for generating a deoxyribonucleic acid (DNA) sequence using the recovered polymer of FIG. 4F.
Figure 7:
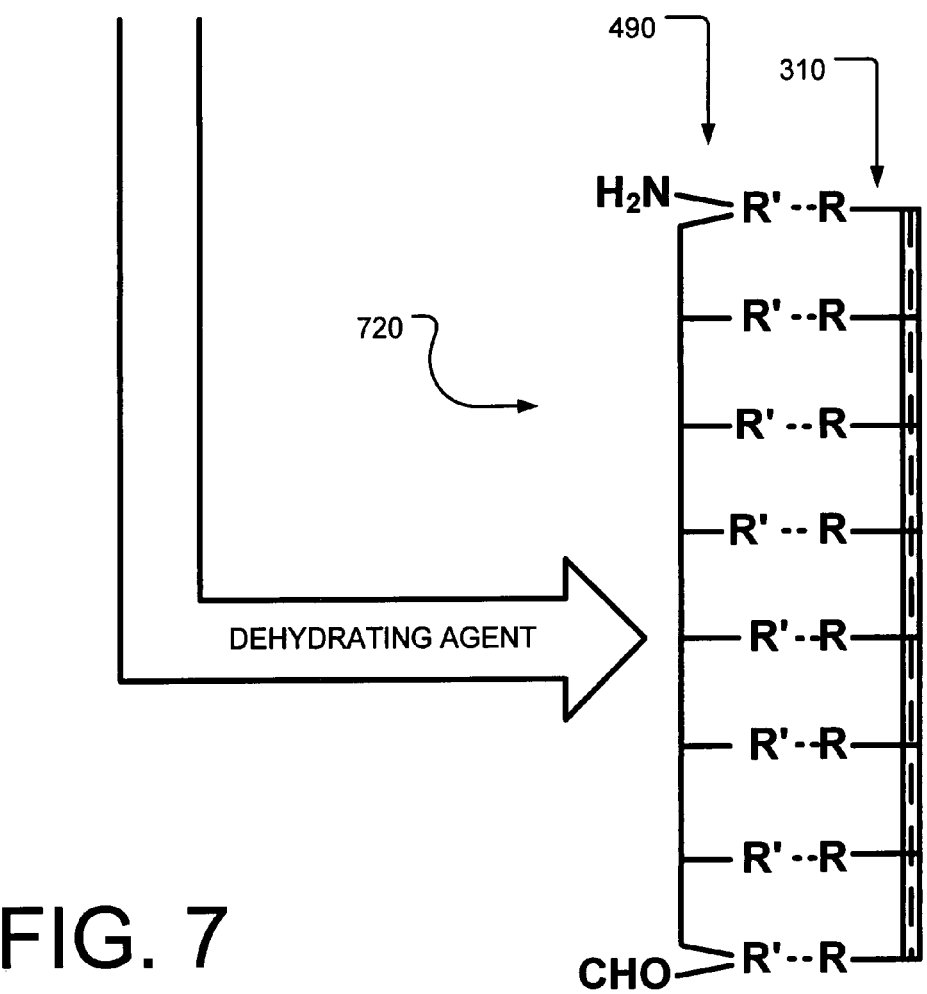

FIG. 7 is a diagram showing an embodiment of a process for reading a DNA sequence using the recovered polymer of FIG. 4F, 5D or 6C. While the embodiment of FIG. 7 uses the polymer of FIG. 4F, it should be appreciated that any of the octamers from the process of FIGS. 5A through 5D and FIGS. 6A through 6C may be used as the template for reading the DNA sequence. In fact, any polymer with a specific sequence and a specific chain length may be used as the template for directing the polymerization process.

As shown in FIG. 7, the synthetic polymer 490 may be used as a template to direct the synthesis of a DNA sequence as shown in by the paper "Catalyst for DNA Ligation: Towards a Two-Stage Replication Cycle," by Ye et al., published in *Angew. Chem. Int. Ed.* 2000, 39, No. 20, which is incorporated herein by reference as if set forth in its entirety. In this regard, when DNA nucleotide monomers 710 are placed in solution with the synthetic polymer 490, the DNA nucleotide monomers 710 assemble in a chain-growth polymerization process in the presence of a dehydrating agent, thereby generating the complementary DNA strand 310. This provides a synthetic replication process without the biological replication machinery. As with biological replication processes, the application of Darwinian selection approaches to this scheme should allow for the in vitro evolution of function and extend the range of sequence-specific polymers far beyond biological polymers. Since these processes should be readily appreciated by those having skill in the art in view of the material disclosed herein, further discussion of such processes is omitted here.

The paper "Expressing Genes Differently," by Li et al., which is fully set forth in U.S. provisional patent application Ser. No. 60/456,641, filed on Mar. 21, 2003, shows several characteristics of the synthetic polymer generated by the processes of FIGS. 4A through 6C. For example, as shown in the paper "Expressing Genes Differently," the above-mentioned monomers and dimers may be used in a 32-mer DNA-catalyzed polymerization reaction to accurately read a sequence of DNA. Since the reaction progresses in an exponential manner (e.g., monomer to dimer, dimer to tetramer, tetramer to octamer, etc.) the efficiency of the polymerization reaction increases with the length of the polymer chain. More importantly, this step-growth process ensures the sequence specificity of template translation, just as the chain-growth polymerization processes which employ the one-by-one addition monomers to the end of the chain, but via kinetic and thermodynamic control of the process as outlined in FIGS. 4A through 6C and the paper "Expressing Genes Differently".

This advantage is more clearly outlined in the paper "Expressing Genes Differently" where 32-mer heteropolymers are translated efficiently into the different backbone products. Moreover, segments of DNA within existing DNA strands may be read easily. Since each of the monomers (or dimers, etc.) has a specific binding site that corresponds to the DNA base pair stretch, these monomers (or dimers, etc.) arrange themselves on the segment of the DNA strand and, through subsequent reduction amination reactions, react to give the complementary strand along the template in a sequence and chain-length specific manner.

Also, unlike the natural phosphate backbone present in DNA, the modified amine backbone on the synthetic polymer has different properties. For example, the synthetic polymer may have a greater affinity to native DNA than other complementary DNA strands. In such circumstances, the displacement of native DNA by the synthetic polymer may inhibit binding by native complementary DNA, thereby controlling the activation or deactivation of certain genes.

Moreover, as shown in the paper "Expressing Genes Differently," while alcohols readily denature DNA duplexes, the synthetic polymer may be more stable in the presence of denaturing solvents due, in part, to the inherent electrostatic attraction of the amine-based backbone and that of the phosphate-based backbone. Furthermore, while it has been shown that a mixed backbone having phosphate and other bases are destabilized, the paper "Expressing Genes Differently" shows that polymers that are devoid of phosphates result in greater stability of polymer duplexes.

Figure 8:
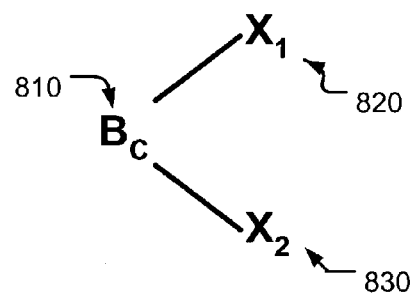
FIG. 8 is a diagram showing one embodiment of a monomer that may be used in polymerization reactions to generate polymers having non-phosphate-based backbones.
Figure 9:
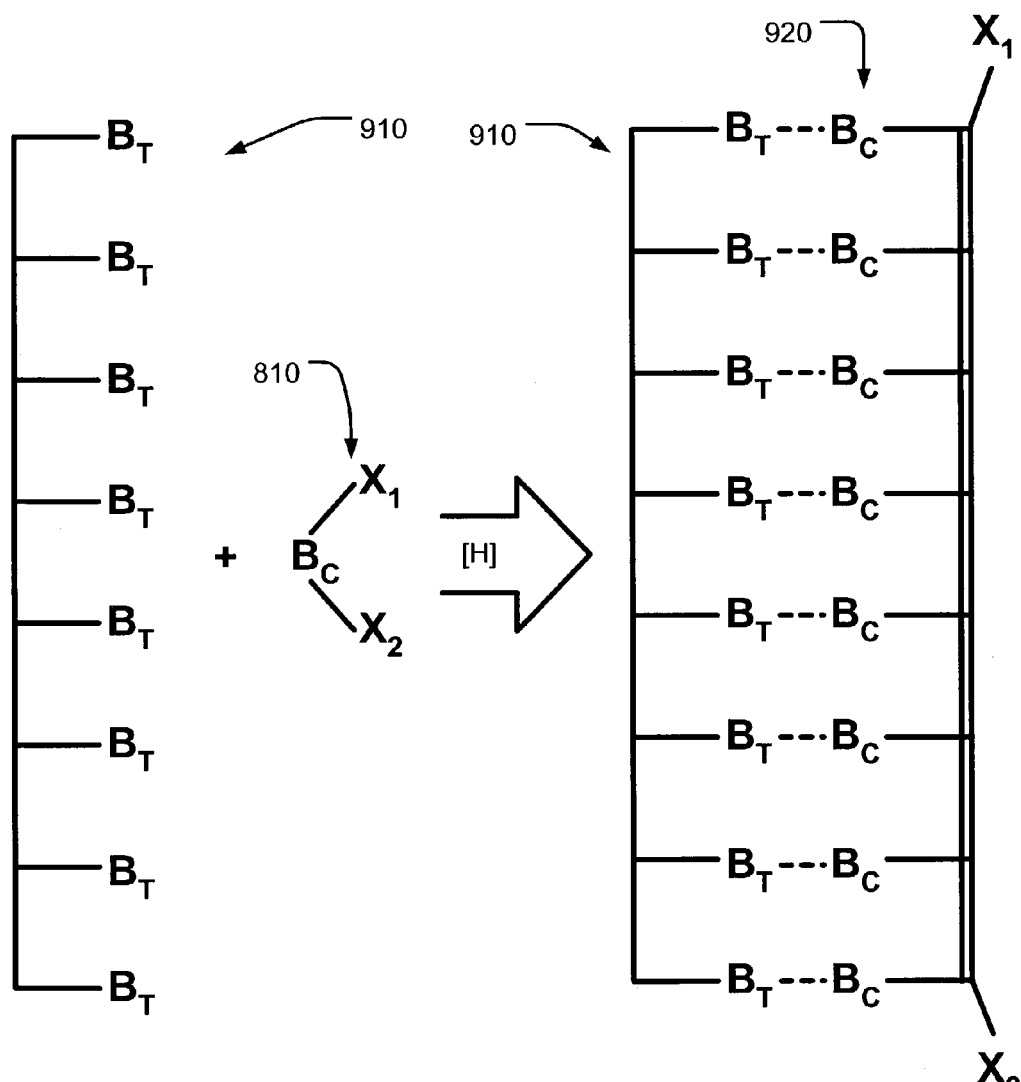
FIG. 9 is a diagram showing one embodiment of a polymerization reaction that generates a polymer having a non-phosphate-based backbone.

Having provided several specific examples of polymerization reactions and related components in FIGS. 1A through 7, a more general application of these principles is provided in FIGS. 8 and 9.

FIG. 8 is a diagram showing a more generalized monomer that may be used in polymerization reactions to generate polymers having non-phosphate-based backbones. Unlike the monomers of FIGS. 1A through 1E, which are largely based on biologically known base pairs and amine-acetaldehyde reactive ends, the monomer of FIG. 8 has a binding site ($B_C$) 810, a first reactive end ($X_1$) 820, and a second reactive end ($X_2$) 830. In one embodiment, a condensation reaction between $X_1$ and $X_2$ in aqueous solution results in the formation of a chemical bond between $X_1$ and $X_2$. In this regard, $X_1$ and $X_2$ may represent an amine/acetaldehyde pairing that results in an imine (as described above), or an amine/carboxylic acid pairing that results in an amide, or an alcohol/carboxylic acid pairing that results in an ester bond. Since these pairings of reactive components are known in the art, only the above truncated discussion is provided to illustrate possible reactants that may be used for $X_1$ and $X_2$.

FIG. 9 is a diagram showing one embodiment of a polymerization reaction that generates a polymer having a non-phosphate-based backbone. As shown in FIG. 9, if a template that has a plurality of binding sites ($B_T$) that are configured to bind with $B_C$, then similar to the reactions outlined in FIGS. 4A through 6C, the attraction between $B_C$ and $B_T$ results in the arranging of monomers along the template 910. Once $B_C$ is aligned along the template 910, the reactivity between $X_1$ of one monomer and $X_2$ of an adjacent monomer results in a condensation reaction, thereby forming a chemical bond between $X_1$ and $X_2$. Additionally, if the reactants $X_1$ and $X_2$ are non-phosphate-based reactants, then the resulting backbone will be a non-phosphate-based backbone. Importantly, $B_T$ is not intended to represent only homopolymers, but heteropolymers as well. Therefore $B_T$ is any sequence of different binding sites each with a specific affinity for a specific $B_C$ monomer.

By increasing the set of polymers to include those that have non-phosphate-based backbones, the possible universe of polymer-based architectures becomes almost limitless.

Although exemplary embodiments have been shown and described, it will be clear to those of ordinary skill in the art that a number of changes, modifications, or alterations may be made, none of which depart from the spirit of the present invention. For example, while known nucleosides (e.g., thymidine, adenosine, guanosine, cytidine, uridine, and inosine) have been used to illustrate the advantages associated with this invention, it should be appreciated that other alternative nucleosides, base pairs, or any molecular recognition element may be used without detriment to the invention. Also, while amines, acetaldehydes, and imines are used to illustrate the polymerization reaction, it should be appreciated that other condensation reactions may also be employed to generate polymers. Moreover, while the several embodiments show the polymerization of monomers, dimers, and tetramers, it should be appreciated that other oligomers (e.g., trimers, pentamers, hexamers, heptamers, octamers, etc.) may be used in the polymerization reaction. Additionally, while homopolymers have been used to simplify the illustration of several embodiments of the invention, it should be appreciated that heteropolymers may be used without adverse effect to the scope of the invention.

Several advantages and characteristics related to the monomers, oligomers, polymers, and the related processes that use these components are shown in the papers included in the above-referenced U.S. provisional patent applications. It should be appreciated that these advantages and characteristics are intended to be within the scope of the disclosure. All such changes, modifications, and alterations should therefore be seen as within the scope of the present invention.

What is claimed is:

1. A template-directed process for synthesizing polymers, the process comprising:
    (a) providing a deoxyribonucleic acid (DNA) template having binding sites, the template further having a specific chain length and a specific sequence; and
    (b) generating a sequence-specific polymer along the DNA template, the sequence-specific polymer having a chain length that corresponds to the specific chain length of the template, the sequence-specific polymer defining a sequence that complements the specific sequence defined by the DNA template, the generating of the sequence-specific polymer comprising:

(b1) providing modified nucleosides having the hydroxyl at the 5'-carbon replaced with an amine, the modified nucleosides further having the hydroxyl at the 3'-carbon replaced with an acetaldehyde;

(b2) pre-arranging the modified nucleosides along the sequence-specific DNA template such that each of the modified nucleosides are bound to their respective complementary binding site on the DNA template;

(b3) forming an imine between adjacent modified nucleosides by reacting the amine of one of the adjacent modified nucleosides with the acetaldehyde of the other of the adjacent modified nucleosides; and (b4) reducing the imine to form an amine between the adjacent modified nucleosides.

2. A template-directed process for synthesizing polymers, the process comprising:

providing at least two nucleosides:

replacing the hydroxyl at the 5' carbon of each of said at least two nucleosides with an amine;

replacing the hydroxyl at the 3' carbon of each of said at least two nucleosides with an acetaldehyde; and generating a polymer along a template polynucleotide through a condensation reaction between the at least two nucleosides.

3. A template-directed process for synthesizing polymers, the process comprising:

providing a template polynucleotide having a specific chain length, the template defining a specific sequence; and generating a product nucleoside polymer along the template through a condensation reaction between two or more nucleosides, each nucleoside having two reactive ends, the product nucleoside polymer having a chain length that corresponds to the specific chain length of the template, the product nucleoside polymer defining a sequence that corresponds to the specific sequence defined by the template.

4. The process of claim 3, wherein the template polynucleotide is a single strand of deoxyribonucleic acid (DNA).

5. The process of claim 3, wherein the template polynucleotide is a single strand of ribonucleic acid (RNA).

6. The process of claim 3, wherein the step of generating a product polymer comprises:

providing modified nucleosides, the modified nucleosides having the hydroxyl at the 5'-carbon replaced with an amine, the modified nucleosides further having the hydroxyl at the 3'-carbon replaced with an acetaldehyde;

arranging the modified nucleosides along the template;

forming an imine between adjacent modified nucleosides along the template, the imine being formed by reacting the amine of one of the adjacent modified nucleosides with the acetaldehyde of the other of the adjacent modified nucleosides; and reducing the imine to form an amine between the adjacent nucleosides.

7. A template-directed process for synthesizing polymers, the process comprising:

providing a template polynucleotide having a specific chain length, the template defining a specific sequence;

providing modified nucleosides, the modified nucleosides having the hydroxyl at the 5'-carbon replaced with an amine, the modified nucleosides further having the hydroxyl at the 3'-carbon repiaced with an acetaldehyde;

arranging the modified nucleosides along the template;

forming an imine between adjacent modified nucleosides along the template, the imine being formed by reacting the amine of one of the adjacent modified nucleosides with the acetaldehyde of the other of the adjacent modified nucleosides; and reducing the imine to form an amine between the adjacent nucleosides.

* * * * *